US006436632B2

(12) United States Patent
Schellenberger et al.

(10) Patent No.: US 6,436,632 B2
(45) Date of Patent: *Aug. 20, 2002

(54) MULTI-THROUGH HOLE TESTING PLATE FOR HIGH THROUGHPUT SCREENING

(75) Inventors: Volker Schellenberger, Palo Alto; Amy Deming Liu, Mountain View, both of CA (US)

(73) Assignee: Genencor International, Inc., Palo Alto, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/970,578

(22) Filed: Oct. 4, 2001

Related U.S. Application Data

(63) Continuation of application No. 09/528,085, filed on Mar. 17, 2000, now Pat. No. 6,306,578, which is a continuation-in-part of application No. 09/471,852, filed on Dec. 23, 1999, now abandoned, which is a continuation of application No. 09/272,122, filed on Mar. 19, 1999, now Pat. No. 6,027,873.

(51) Int. Cl.[7] ............................ C12Q 1/00; C12Q 1/02; C12Q 1/24
(52) U.S. Cl. ..................... 435/4; 435/283.1; 435/29; 435/30; 422/50; 422/68.1
(58) Field of Search ................. 435/4, 283.1, 29, 435/30; 422/50, 68.1

(56) References Cited

U.S. PATENT DOCUMENTS

| 4,493,815 A | 1/1985 | Fernwood et al. | 422/101 |
|---|---|---|---|
| 4,834,946 A | 5/1989 | Levin | 422/101 |
| 5,000,921 A | 3/1991 | Hanaway et al. | 422/100 |

(List continued on next page.)

FOREIGN PATENT DOCUMENTS

| WO | WO 97/37036 | 10/1997 |
| WO | WO 99/34920 | 7/1999 |
| WO | WO 00/56456 | 9/2000 |

OTHER PUBLICATIONS

Arndt et al., A Rapid Genetic Screening System for Identifying Gene–Specific Suppression Constructs for use in Human Cells, *Nucleic Acids Research*, vol. 28, No. 6., pp. e15–i–viii (2000).
Rolls et al., A Visual Screen of GFP–Fusion Library Identifies a New Type of Nuclear Envelope Membrane Protein, *J. Cell Biol.*, vol. 146, No. 1, pp. 29–43 (1999).
Sieweke, Direction of Transcription Factor Partners with a Yeast One Hybrid Screen, *Methods Mol. Biol.*, vol. 130, pp. 59–77 (2000).
Zhao et al., Directed Evolution Converts Subtilisin E into a Functional Equivalent of Thermitase, *Protein Eng.*, vol. 12, No. 1, pp. 47–53 (1999).

*Primary Examiner*—Louise N. Leary
(74) *Attorney, Agent, or Firm*—Kilyk & Bowersox, P.L.L.C.

(57) ABSTRACT

A method for holding samples for analysis and an apparatus thereof includes a testing plate with a pair of opposing surfaces and a plurality of holes. Each of the holes extends from one of the opposing surfaces to the other one of the opposing surfaces. The holes are arranged in groups, where each group has at least two rows and two columns of holes. The groups are arranged in sets, where each set has at least two rows and two columns of groups. To analyze samples, at least one of the opposing surfaces of the testing plate is immersed in a solution to be analyzed. A portion of the solution enters openings for each of the holes in the immersed opposing surface. Once the holes are filled with solution, the testing plate is removed and is held above a supporting surface. Surface tension holds the solution in each of the holes. The solution in one or more of the holes is then analyzed and the solution in one of these holes is identified for further study. The location of the identified solution is marked based upon its location within a particular set and group of holes.

81 Claims, 6 Drawing Sheets

U.S. PATENT DOCUMENTS

| | | | |
|---|---|---|---|
| 5,047,215 A | 9/1991 | Manns | 422/101 |
| 5,108,704 A | 4/1992 | Bowers et al. | 422/70 |
| 5,210,021 A | 5/1993 | Goodwin, Jr. | 435/29 |
| 5,262,128 A | 11/1993 | Leighton et al. | 422/100 |
| 5,284,753 A | 2/1994 | Goodwin, Jr. | 435/30 |
| 5,506,141 A | 4/1996 | Weinreb et al. | 435/309.1 |
| 5,560,811 A | 10/1996 | Briggs et al. | 204/451 |
| 5,763,263 A | 6/1998 | Dehlinger | 435/287 |
| 5,770,440 A | 6/1998 | Berndt | 435/288.4 |
| 5,849,598 A | 12/1998 | Wilson et al. | 436/180 |
| 6,027,873 A * | 2/2000 | Schellenbergerr et al. | 435/4 |
| 6,306,578 B1 * | 10/2001 | Schellenberger et al. | 435/4 |

\* cited by examiner

US 6,436,632 B2

MULTI-THROUGH HOLE TESTING PLATE FOR HIGH THROUGHPUT SCREENING

CROSS REFERENCE TO THE RELATED APPLICATIONS

The present application is a continuation of prior U.S. patent application Ser. No. 09/528,085, filed Mar. 17, 2000, now U.S. Pat. No. 6,306,578, which in turn is a continuation-in-part of prior U.S. patent application Ser. No. 09/471,852, filed Dec. 23, 1999, now abanadoned which in turn is a continuation of U.S. patent application Ser. No. 09/272,122, filed Mar. 19, 1999, now U.S. Pat. No. 6,027,873 all of which are herein incorporated in their entireties by reference.

FIELD OF THE INVENTION

This invention is related generally to a testing apparatus and, more particulary, to a multi-through hole testing plate for high throughout screening.

BACKGROUND OF THE INVENTION

Prior testing apparatuses have consisted of a testing plate with a pair of opposing surfaces and plurality of wells. The wells extend in from one of the opposing surfaces, but do not extend through to the other opposing surfaces. The wells are used to hold samples of solution to be analyzed.

Although these testing apparatuses work there are some problems. For example, the wells in these testing apparatuses are difficult to fill. Special delivery systems, such as large pipette systems, are needed to fill each of the wells with samples of solution. These special delivery systems are often expensive and difficult to operate. As a result, the overall cost of the testing procedure is increased.

Another problem with these prior testing apparatuses is with their construction. The bottom of the wells in these testing plates need to be transparent so that light can be transmitted through the samples during testing. However, the rest of the testing plate needs to be constructed of a non-transparent material. The construction of a testing apparatus with these characteristics is difficult and expensive.

Yet another problem with these prior testing apparatuses is with the operator locating a particular well in the testing apparatus. Typically, these testing apparatuses each include large numbers of wells which are equidistantly spaced apart. As a result, locating a particular well within the large number of wells is difficult.

Accordingly, there is a need for an improved testing apparatus for high throughput screening.

SUMMARY OF THE INVENTION

A method for holding samples in accordance with one embodiment of the present invention includes several steps. First, a testing plate with a pair of opposing surfaces and a plurality of holes is provided. Each of the holes extends from one of the opposing surfaces to the other one of the opposing surfaces. Next, at least one of the opposing surfaces of the testing plate is immersed in a solution to be analyzed. A portion of the solution enters openings for each of the holes in the immersed opposing surface and any gases in the holes escape though openings for each of the holes in the other opposing surface. Next, the testing plate is removed from the solution. Surface tension holds some of the solution in each of the holes. The opposing surfaces of the testing plate are then held above a supporting surface and the solution held in at least one of the holes is analyzed.

A method for identifying the location at least one sample of a solution in accordance with another embodiment of the present invention includes several steps. First, a testing plate with a pair of opposing surfaces and a plurality of holes is provided. Each of the holes in the testing plate extend from one of the opposing surfaces to the other one of the opposing surfaces. The holes in the plate are arranged in groups. Each of the groups comprises at least two rows and two columns of holes. Once a testing plate has been provided, solution is loaded into the holes and is then analyzed. Based on this analysis, the solution in at least one hole is identified for further study. The location of the identified hole is marked based upon the group in which the hole is found.

A method for screening a sample in accordance with another embodiment of the present invention includes several steps. First, a solution of the sample is prepared for screening. Next, a testing plate with a pair of opposing surfaces and a plurality of holes is provided. Each of the holes extends from one of the opposing surfaces to the other one of the opposing surfaces in the testing plate. Next, at least one of the opposing surfaces of the testing plate is immersed in a solution. A portion of the solution enters openings for each of the holes in the immersed opposing surface of the testing plate. Once the solution has enter into the holes, the testing plate is removed from the solution and the surface tension holds at least some of the solution in the holes. Next, the solution in one or more of the holes is analyzed.

An apparatus for holding samples of a solution with cells for analysis in accordance with another embodiment of the present invention includes a testing plate with a pair of opposing surfaces and a plurality of through holes. Each of the holes extends from an opening in one of the opposing surfaces in the testing plate to an opening in the other one of the opposing surfaces and is sized to hold a plurality of the cells. A portion of at least one of the opposing surfaces of the testing plate where the holes are located is recessed so that the openings in the testing plate are spaced in from the opposing surface.

An apparatus for holding samples for analysis in accordance with yet another embodiment of the present invention also includes a testing plate with a pair of opposing surfaces and a plurality of holes. Each of the holes extends from one of the opposing surfaces to the other one of the opposing surfaces. The holes are arranged in groups on the testing plate, where each of the groups comprises at least two rows and two columns of holes.

The method and apparatus for holding samples for analysis in accordance with the present invention provides a number of advantages. For example, the present invention simplifies testing procedures. The samples of solution to be analyzed can be loaded into the testing plate by simply dipping or flooding one of the surfaces of the testing plate into the solution. As a result, the present invention does not require the use of a separate delivery systems for loading solution into the wells on the testing plate.

The present invention also simplifies the construction of the testing apparatus. The testing apparatus merely needs one of the opposing surfaces of the testing apparatus to be spaced away by additional spacers or machined to create a recessed portion and then a plurality of holes need to be drilled through the plate in the recessed portion. Unlike prior testing apparatuses, the present invention does not require any special construction techniques to male the bottom of the wells transparent because the holes extend all of the way through the plate.

The present invention also permits an operator to more easily identify a particular hole filled with a sample for further analysis. Instead of spacing the holes equidistantly over the testing plate, the present invention arranges the holes in groups of at least two columns and two rows of holes and arranges the groups in sets of at least two or more. The groups are spaces further apart then the holes within each group and sets of groups are spaced further apart then the groups are spaced apart. As a result, an operator can more easily identify a particular hole based upon which set, group, row, and column the hole is located in on the testing plate.

DETAILED DESCRIPTION

Figure 1:
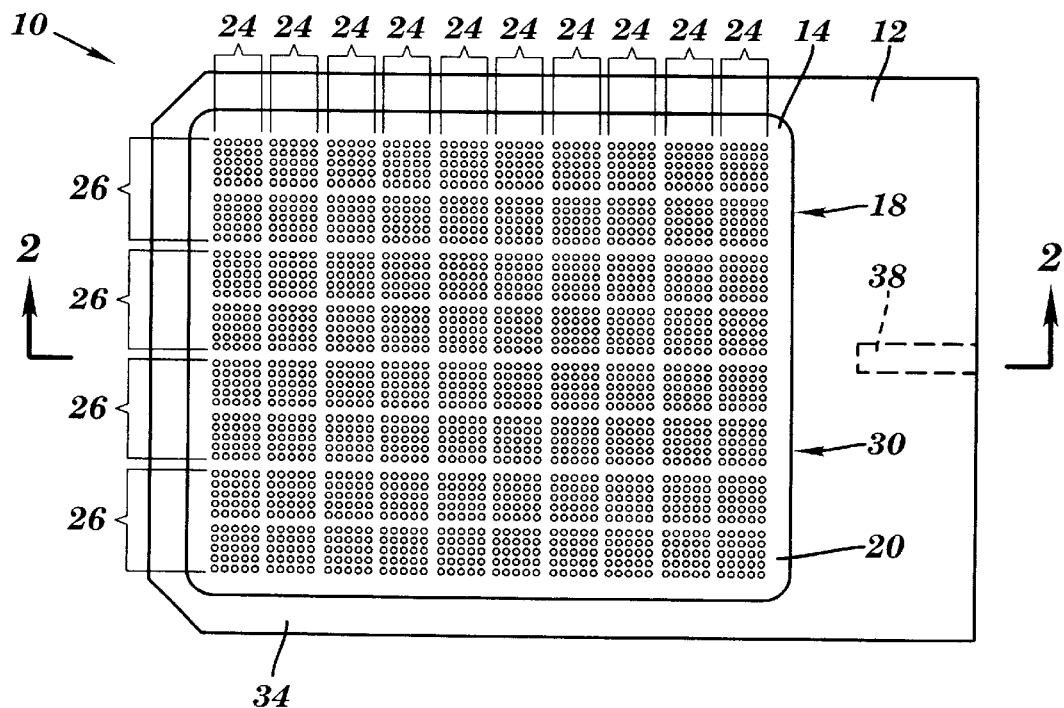
FIG. 1 is a top view of a multi-through hole testing plate in accordance with one embodiment of the present invention.
Figure 2:
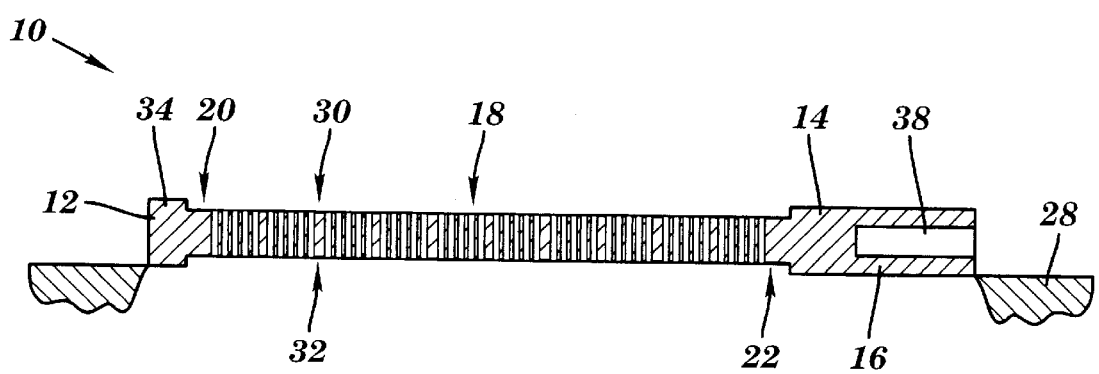
FIG. 2 is a cross-sectional view of the multi-through hole testing plate shown in FIG. 1 taken along lines 2—2.

A testing apparatus 10 in accordance with one embodiment of the present invention is illustrated in FIG. 1. The testing apparatus 10 includes a testing plate 12 with a pair of opposing surfaces 14 and 16 (surface 16 is shown in FIG. 2) and a plurality of through holes 18. The through holes 18 are located in recessed portions 20 and 22 on each side of the testing plate 12. The through holes 18 are also arranged in groups 24 of at least two columns and two rows of holes 18 and in sets 26 of two or more groups of holes 18. The testing apparatus 10 provides a number of advantages including simplifying the procedure for loading samples of solution S into the holes 18 in the testing apparatus 10, simplifying the construction of the testing apparatus 10, and making the identification of a particular hole 18 filled easier for an operator.

Referring to FIGS. 1 and 2, the testing apparatus 10 includes the testing plate 12 which in this particular embodiment is made of a non-transparent material, such as aluminum and polypropylene, although other types of materials, such as teflon, polystyrene, stainless steel, polythylene, any metal or plastic, can be used. The testing plate 12 could also be made of transparent materials, such as glass of transparent plastic, when non-optical means are used for analysis, such as analyzing the materials blotted on membranes.

The testing plate 12 includes the pair of opposing surfaces 14 and 16. In this particular embodiment, the opposing surfaces 14 and 16 are substantially planar, except where the recessed portions 20 and 22 are located, although the surfaces 14 and 16 could have other relationships with respect to each other. Each of the opposing surfaces 14 and 16 includes one of the recessed portions 20 and 22 which are machined into the testing plate 12, although other techniques for forming the recessed portions 20 and 22, such as by molding or adding spaces, can be used. When either of the opposing surfaces 14 and 16 of the testing plate 12 rests on a supporting surface 28, the recessed portion 14 or 16 along with the plurality of holes 18 located in the recessed portion 14 or 16 are spaced away from the supporting surface 28. If openings 30 and 32 to the holes 18 contacted the supporting surface 28, then any solutions in the holes 18 would drain out of the holes 18. In this particular embodiment, a ridge 34 if formed in each of the opposing surfaces 14 and 16 by the recessed portions 20 and 22 which extends around the outer circumference of the testing plate 12. Although the holes 18 are spaced from the support surface 28 by a recessed portion 20 or 22 formed in the testing plate 12, the holes 18 can be spaced from the supporting surface 28 with other types of supporting structures, such as a bracket attached to the testing plate which supports the testing plate 12 and holes 18 above the supporting surface 28.

Figure 5:
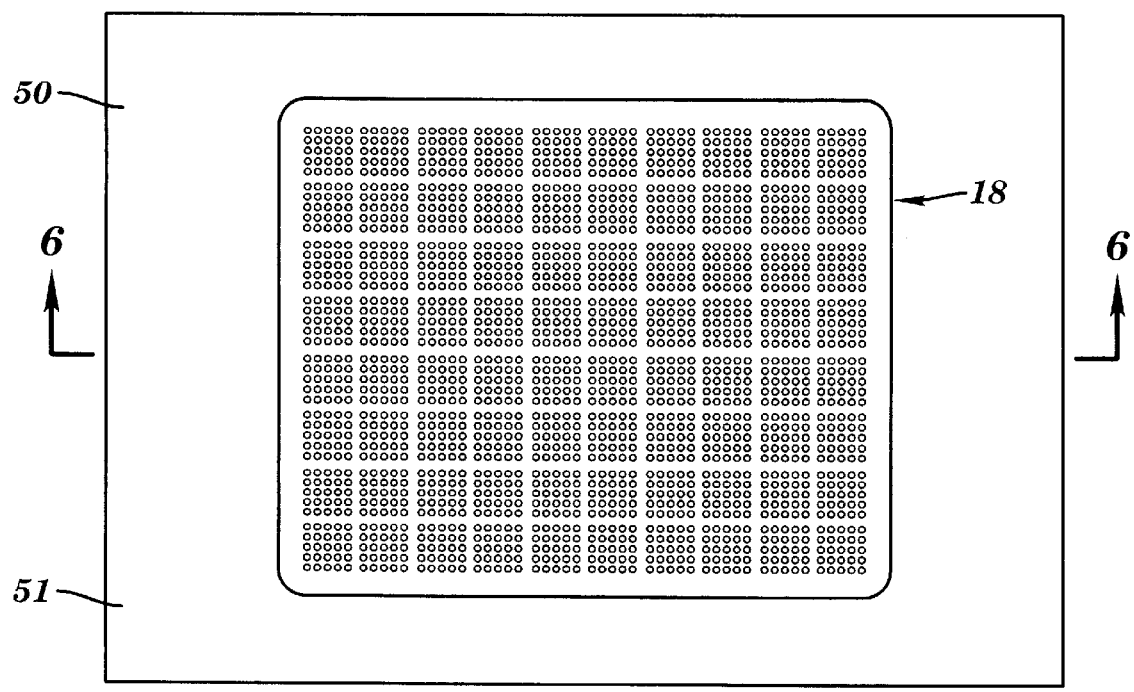
FIG. 5 is a top view of the multi-through hole testing plate in accordance with another embodiment of the present invention.
Figure 6:
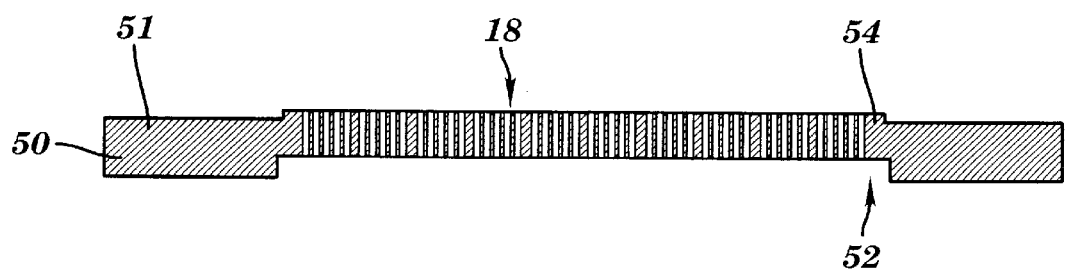
FIG. 6 is a cross-sectional view of the multi-through hole testing plate shown in FIG. 5 taking along the lines 6—6.

Referring to FIGS. 5 and 6, another testing apparatus 50 in accordance with one embodiment of the present invention is illustrated. The testing apparatus 50 is identical to the test apparatus 10 shown in FIGS. 1 and 2 except that the testing apparatus 50 does not include a pair of recessed portions. Instead, the testing apparatus 50 has a recessed portion 52 and a protruding portion 54. When the testing plate 51 is placed on a supporting surface, the recessed portion 52 must be facing the supporting surface so that the holes are spaced from the supporting surface. Although one example of the testing apparatus 50 is shown, the opposing surfaces of the testing plate 51 could have other configurations. For example, protruding portion 54 could be made flush with the upper surface of testing plate 51.

Figure 3:
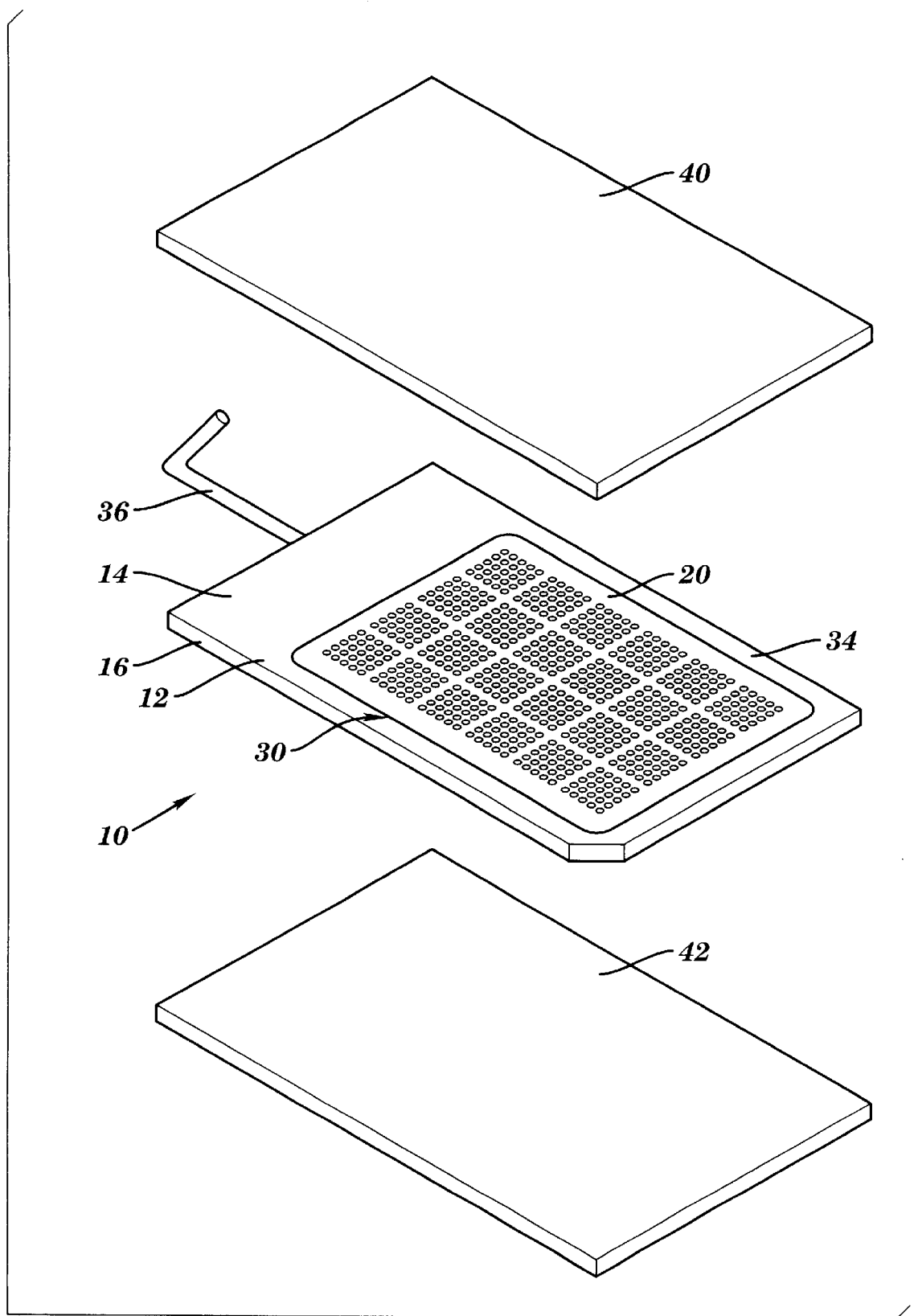
FIG. 3 is a perspective, exploded view of another multi-through hole testing plate in accordance with the present invention between a pair of evaporation plates.

Referring to FIGS. 1–3, the testing plate 12 also includes an optional handle 36 and an opening 38 on one side of the testing plate 12 to receive one end of the handle 36, although other techniques for connecting the handle 36 to the testing plate 12 can be used, such as connecting the handle 36 with bolts. The handle 36 extends out from the side of the testing plate 12 and is used to maneuver the testing plate 12 during loading and testing.

Figure 4:
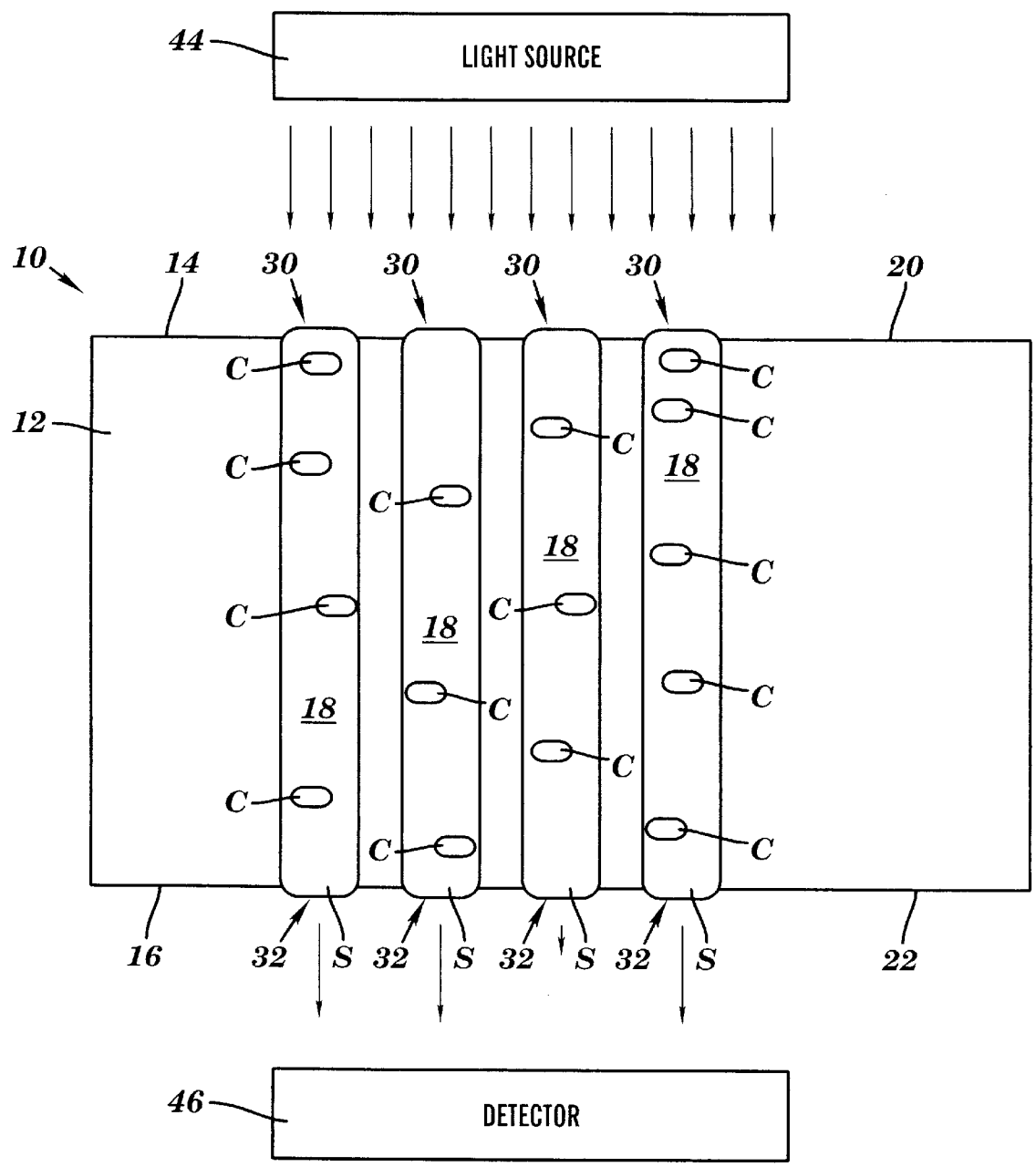
FIG. 4 is a block diagram of a testing apparatus with a multi-through hole testing plate in accordance with another embodiment of the present invention.

A plurality of through holes 18 are located in the testing plate 12. The holes 18 extend from openings 30 in the recessed portion 20 of one of the opposing surfaces 14 to openings 32 in the recessed portion 22 of the other opposing surface 16. In this particular embodiment, the holes 18 have a substantially cylindrical shape, although the holes 18 could have other shapes, such as a hexagonal cross-sectional shape or a cone shape. In this particular embodiment, each of the holes 18 has a diameter of about one millimeter and can hold about hold about 5.5 microliters of solutions S and cells C, although the diameter, volume and number of cells C each hole 18 can hold can vary as needed or desired. The solution S along with cells C in the solution S are held in the holes 18 by surface tension as shown in FIG. 4. More specifically, the size of the holes 18 may need to change depending upon the solution S to be analyzed and that solution's surface tension properties. For example as understood by one of ordinary skill in the art, a buffer solution might have different surface tension properties than a culture media containing salt. There must be sufficient surface tension to keep the samples of solution S in the holes 18.

One of the advantages of the present invention is that the testing plate 12 is easy to manufacture. A plate having opposing surfaces can have an appropriate number of holes drilled there through. The plate can include one or more recessed portions 20, 22, and the through holes can pass through the recessed portion of the plate 12. Since the holes 18 extend all of the way through, there is no need for a transparent bottom in each hole 18. Light transmitted into the holes 18 will pass through during testing. With prior wells, the testing apparatus also needed to be non-transparent, but since the wells did not extend through the apparatus, the bottom of the wells needed to be made of a transparent material to permit light to pass through the sample for optical analysis. Constructing these prior testing apparatuses was difficult and expensive.

Referring to FIG. 1, the testing plate 12 has about two-thousand holes 18 which extend through from one opposing surface 14 to the other opposing surface 16, although the number of holes 18 can vary as needed or desired. To assist an operator in identifying a particular hole 18 in this particular embodiment the holes 18 are arranged in groups and sets of holes 18. Each group 24 contains at least two rows and two columns of holes 18 and each set 26 includes at least two rows and two columns of groups 24. In this particular embodiment, each group 24 of holes 18 and five rows and five columns of holes 18 and there are eighty groups 24 of twenty-five holes 18 in this example, although the number can vary as needed or desired. The holes 18 in this example are spaced about 1.5 mm apart between rows of holes 18 and between columns of holes 18 within each group 24, although this distance can vary and the spacing between rows of holes 18 and columns of holes 18 within each group 24 can be different as needed or desired. In this particular embodiment, each set of groups 24 includes two rows of groups 24 and ten rows of groups 24 and there are four sets 26 which contain twenty groups 24 of holes 18 each in this example, although the number can vary as needed or desired. The groups 24 within a set 26 in this example are spaced about 2.0 mm apart and the sets 26 of groups 24 of holes 18 in this example are spaced about 2.5 mm apart, although these distances can vary as needed or desired.

By arranging the holes 18 in sets 26 and groups 24, it is much easier for an operator to identify a particular hole 18 in the testing plate 12 and retrieve a particular sample. The sets 26 of holes 18 help the operator identify the general area of the hole 18 and then the groups 24 help the operator to begin to narrow down the location of the hole 18. The column and row of the hole 18 in each group 24 provides the precise location of the hole 18. The spacing between sets 26, groups 24, and rows and columns are different to make it visually easier for an operator to identify a particular hole 18. When the holes 18 are all spaced equidistantly apart, then it is more difficult to identify a particular hole 18 and it is easier for an operator to lose his/her place and select a sample from the wrong hole 18.

Figure 7:
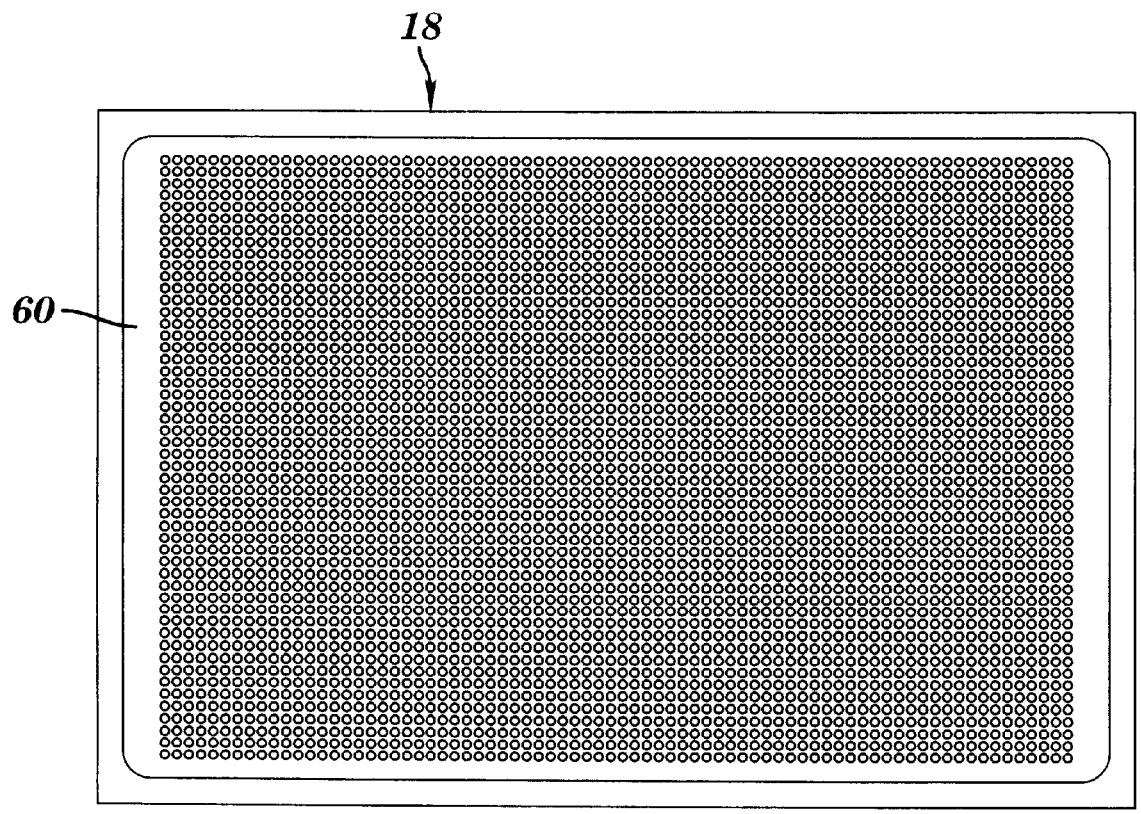
FIG. 7 is a top view of a multi-through hole testing plate in accordance with yet another embodiment of the present invention.

Although the holes 18 are arranged in groups 24 and sets 26 in testing apparatuses 10 and 50 to aid human operators, other arrangements for the holes 18 may also be used. For example, when the testing apparatuses are used by robotics, instead of human operators, the holes 18 can also be spaced equidistantly apart as shown in the embodiment of the testing apparatus 60 illustrated in FIG. 7. The testing apparatus 60 is identical to the testing apparatuses 10 and 50 described and illustrated earlier except for the that the holes 18 are equidistantly spaced apart.

Referring to FIG. 3, the testing apparatus 10 may also include a pair of optional evaporation plates 40 and 42. The evaporation plates 40 and 42 are each secured to the one of the opposing surfaces 14 and 16 of the testing plate 10. The evaporation plates 40 and 42 are secured to the testing plate 12 by bolts, clamps, or other mechanical means. When the evaporation plates 40 and 42 are secured to the testing plate 12 over the recessed portions 20 and 22, the recessed portions 20 and 22 in the opposing surfaces 14 and 16 of the testing plate 12 still space the openings 30 and 32 of the through holes 18 away from the evaporation plates 40 and 42. The evaporation plates 40 and 42 help to preserve the samples of solution S in the holes 18 in the testing plate 12 from evaporation and contamination.

Instead of a recessed portion in the plate 12, an assembly comprising the plate and evaporation plates can be provided with spacers between the testing plate and the evaporation plates to space the openings of the through holes away from the evaporation plates. The evaporation plates could be provided with recesses portions in addition to, or instead of, spacers between the testing plate and the evaporation plates. Any combination of recessed portions in the testing plate, recessed portions in the evaporation plates, or spacers can be used to provide the spacing between the openings of the through holes and the evaporation plates.

According to an embodiment of the present invention, stackable testing plates are provided which may or may not have evaporation plates in-between testing plates. The stackable testing plates may be provided with recessed portions or evaporation plates with recessed portions can be provided between a stacked testing plate. Any combination of recessed portions in the testing plates, recessed portions in the evaporation plates, or spacers can be used to provide a stack of testing plates wherein each testing plate is spaced from the surface of an adjacent testing plate, evaporation plate, or both.

One example of one application of the present invention will be discussed with reference to testing apparatus 10 shown in FIGS. 1–4. In this particular example, cells C are mutagenized using ultraviolet, chemical mutagenesis, or other mutagenesis technology. The cells C are grown to allow for segregation. Once the cells C have grown, the cells C are diluted to one cell C per ten microliters in a medium containing a fluorgenic or chromogenic substrate. For purposes of this example, the medium with the cells C is referred to as the solution S. As a result, the cells will be randomly distributed in the holes 18 and many of the holes 18 will contain one or more cells C.

Although one example of preparing the solution S and cells C is disclosed, other methods and techniques for preparing samples to be used with the testing apparatus 10 can be used as is readily understood by one of ordinary skill in the art.

Next, a testing plate 12 with a pair of opposing surfaces 14 and 16 and a plurality of holes 18 which extend from one of the opposing surfaces 14 to the other one of the opposing surfaces 16 is provided. At least one of the opposing surfaces 14 of the testing plate is immersed in the prepared solution S. The solution S enters openings 30 and 32 for each of the holes 18 in testing plate 12 and any gases in the holes 18 may escape through openings 30 and 32 at the opposite end of the holes 18. Alternatively, the testing plate 12 may be flooded with solution S so that the solution S enters through the top opening 30 to each hole 18.

One of the advantages of the present invention is the ease with which solution S can be loaded into each of the holes 18. As illustrated in the description above, all of the holes 18 in the testing plate 12 can be loaded with samples of solution S in a relatively short period of time and without any type of specialized solution delivery system. Prior testing apparatuses with wells required specialized solution delivery system, such as large pipette devices, to be able to load solution into each of the wells. These specialized solution delivery systems are difficult to use and are expensive.

Once the solution S has been drawn into the holes 18, the testing plate 12 is removed from the solution S. Surface tension holds the solution S in each of the holes 18. In this particular embodiment, each hole 18 has a diameter of about one millimeter and holds about 5.5 microliters of solution S and cells C as shown in FIG. 4, although the diameter and volume of each hole 18 can vary as needed or desired for the particular application. The handle 36 can be used to manipulate the position of the testing plate 12 during the above-described operations.

Once the testing plate 12 is removed from the solution S, the testing plate 12 can be placed on a supporting surface 28. Since the holes 18 are located in a recessed portion 22 of the testing plate 12, the openings 22 to the holes 18 are spaced from the supporting surface 28 so that any solution S being held by surface tension remains in the holes 18. A pair of evaporation plates 40 and 42 may be attached to the opposing surfaces 14 and 16 of the testing plate 12 to prevent the samples of solution S in the testing plate 12 from evaporating or becoming contaminated.

In this particular example, the testing plate 12 is then optionally incubated at a controlled temperature of about 37° C. and a humidity of about 70%, although the temperature and humidity will vary based upon the particular application. During the incubation, the cells multiply and produce a protein of interest (the cells could produce an enzyme, an antibody, or a metabolite which could be of interest). The ability of the protein, such as an enzyme, to hydrolyze a substrate is analyzed, such as by measurement of fluorogenic or chromogenic groups liberated by the hydrolysis.

Although one example of processing the samples of solution S in the testing plate 12 is disclosed, other methods and techniques for processing and analysis the samples can also be used and are know to those of ordinary skill in the art.

Next, in this particular example the samples of solution S with cells C in the holes 18 (as shown in FIG. 4) are tested using an image analyzer with a light source 44 and a detector 46 in this particular example. Light is transmitted from the light source 44 towards the openings 30 for the holes 18 in the testing plate 12 and through the solution S in the holes 18 of the testing plate 12. The detector 46 is positioned on the opposing side of the testing plate 12 and detects the light which has been transmitted through the solution S in the holes 18. Based upon the changes in the detected light from the transmitted light, information about the characteristics of the particular samples of solution S can be determined in a manner well known to those of ordinary skill in the art. In this particular example, the image analyzer is able to determine which holes 18 contain solution S with the highest concentration of converted substrate and consequently the highest amount of enzyme. The target in this case is to retrieve the cells C which produced the largest amount of enzyme. In a similar way, cells C which produced the largest amount of a protein or a chemical of interest could be identified.

Although one example of analyzing the samples of solution S in the testing plate 12 using optics is disclosed, other methods and techniques for analyzing the samples, such as non-optical methods, can also be used. For example, a plate containing samples of solution S with cells C could be blotted onto a membrane and used for performing Western blot analysis or alternatively, the samples S with cells C could be blotted onto substrate containing material whereby modification of the substrate is measured visually. As a result, when non-optical means are used to analyze the samples of solution in the testing plate 12, the testing plate 12 can be made of a transparent material.

Next, in this particular example the operator retrieves the samples of solution S which contain the highest concentration of converted substrate. The holes 18 with the solution S with the highest concentration of converted substrate can be identified and located based upon which set 26 of groups 24, which group 24, and which row and column within each group 24 each identified hole 18 is located. One of the advantages of the present invention is the arrangement of the holes in groups 24 and sets 26 which enables an operator to easily identify a particular hole 18 on the testing plate 12. Once the desired samples are retrieved, the operator can conduct further analysis on those samples in manners well known to those of ordinary skill in the art.

Although one example of retrieving one or more of the samples of solution S in the testing plate 12 is disclosed, other methods and techniques for retrieving samples can also be used. For example, if robotics are used to located and retrieve a particular sample, a different testing apparatus, such as testing apparatus 60 shown in FIG. 7, could be used. The robotics would not need the holes 18 to be arranged in groups 24 and sets 26 of holes 18, although such an arrangement may even aid the robotics in identifying and retrieving the desired sample.

According to some embodiments of the present invention, the testing plate is in the form of an assembly or substrate. For example, the plate can comprise a plurality of individual components which together make up an assembly having opposing surfaces and a plurality of through holes extending from one surface to the other. An example of the present invention wherein the testing plate comprises such an assembly is a plate made of a bundle of capillary tubes as shown in FIGS. 8 and 9.

Figure 8:
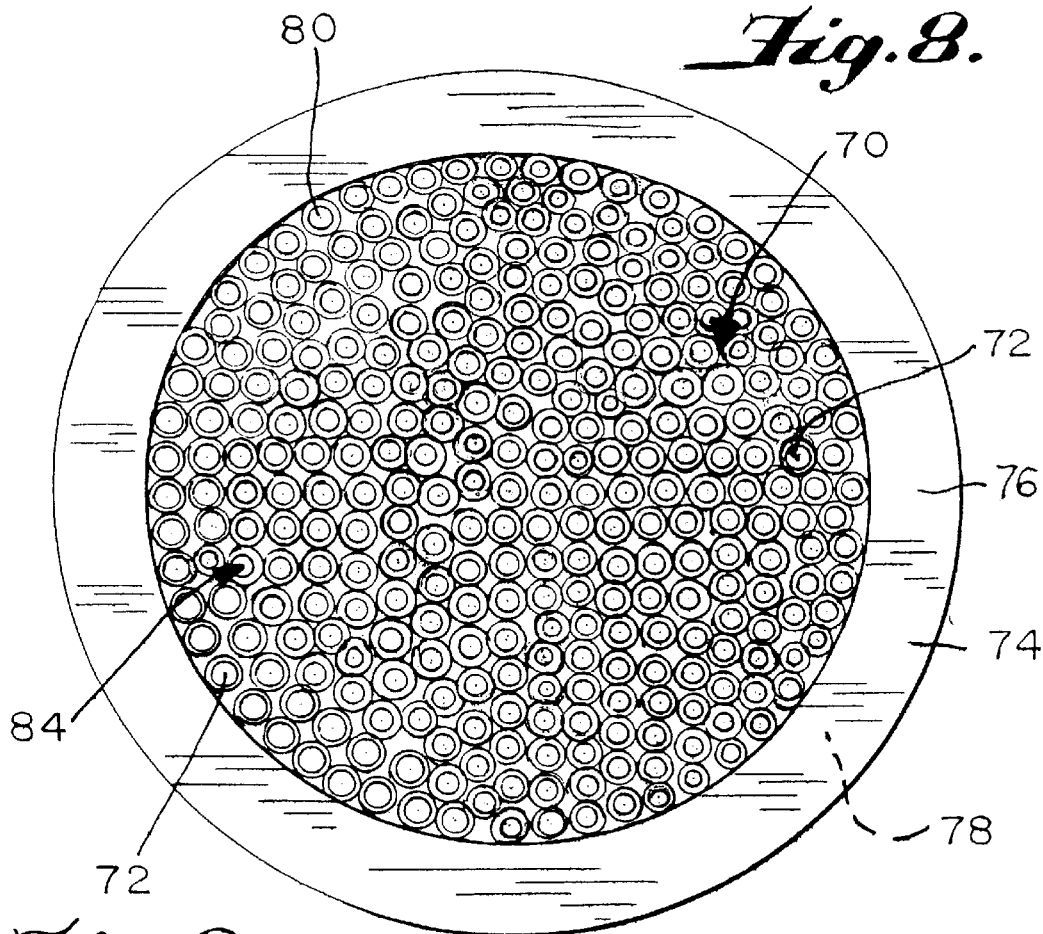
FIG. 8 is a top view of a testing plate assembly according to an embodiment of the present invention.
Figure 9:
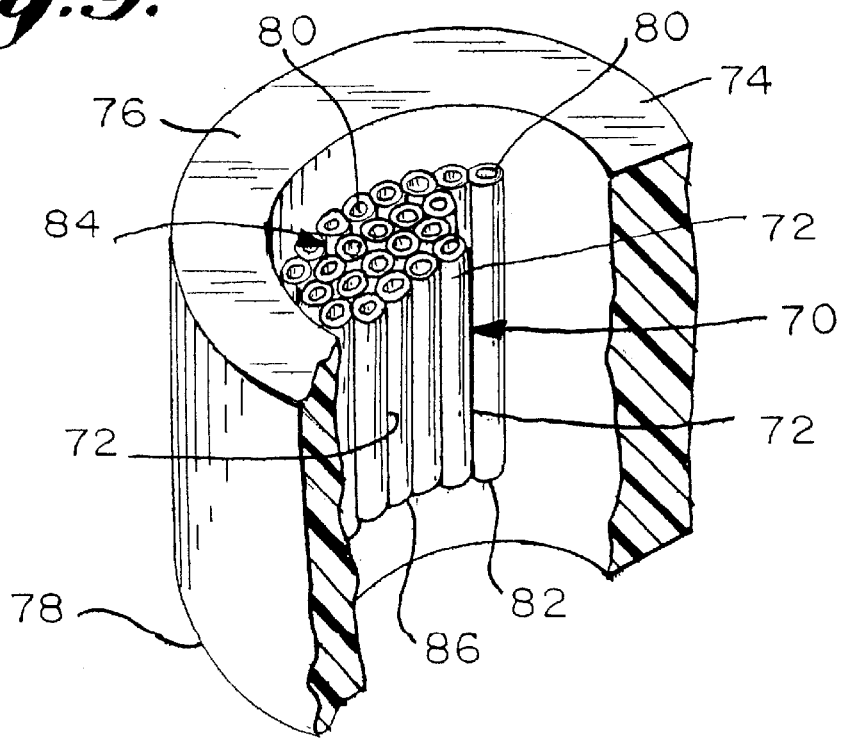
FIG. 9 is a perspective view of the assembly of FIG. 8 shown in partial cut-away.

As shown in FIGS. 8 and 9, a plate, substrate or assembly 70 comprises a bundle of capillary tubes 72 bound together by a band 74. The through holes of the assembly according to this embodiment are the longitudinally-extending holes through the center of each capillary tube. The band 74 may have opposing surfaces 76 and 78, each of which is substantially planar and substantially parallel to the other. The band can be made of metal, plastic, glass, rubber, elastomeric compound, or any other suitable material. Each capillary tube 72 has a first end 80 and a second end 82. The first ends 80 of the capillary tubes make up an opposing surface 84 of the substrate or assembly 70 and the second ends 82 of the capillary tubes 72 made up an opposing surface 86 of the substrate or assembly.

As can be seen in FIGS. 8 and 9, each capillary tube 72 of the bundle which makes up substrate or assembly 70 has a length between its first end 80 and its second end 82 which is at least two times greater than the average diameter of each tube. Preferably, the length of each tube is more than four times greater than the average diameter of each tube and is preferably many times greater than the average diameter. Each capillary tube may be, for example, in the form of a microcapillary tube or a hollow fiberoptic fiber.

The capillary tubes may be hollow cylindrical in shape or may have other rounded, oval, or polygonal cross-sections. The average diameter of each capillary tube preferably ranges from about 0.001 millimeter to about 1 millimeter, and the length of each tube preferably ranges from about 1 mm to about 1 cm. The dimensions of the capillary tubes are preferably such that each tube has the capacity to hold from about 0.0001 microliter to about 10 microliters of liquid sample, for example, about 5.5 microliters, although the diameters, lengths, and holding capacities of the capillary tubes may vary as needed or desired. According to some embodiments of the present invention, it is not necessary to have a band for holding the capillary tubes together in a bundle as the tubes may instead be fused or otherwise bonded, adhered, or maintained together in a bundle.

The number of capillary tubes of the embodiment in FIGS. 8 and 9 is preferably from about 100 to over 1,000 capillary tubes, for example, from about 500 to about 1,500. Preferably, the tubes are arranged in rows and preferably the rows are arranged in columns. Although in the embodiment shown in FIGS. 8 and 9 the bundle of capillary tubes 72 has a circular cross-section and the band 74 is ring shaped, other shapes of the bundle and band are also within the scope of the present invention. For example, a rectangular or square array of capillary tubes can be provided and surrounded by a band, and the band would also preferably be of rectangular or square shape. With rectangular or square-shaped arrays of capillary tubes, distinct columns and rows of capillary tubes can be easily identified, facilitating the identification of a single capillary tube within the array.

In embodiments such as the one shown in FIGS. 8 and 9, the band 74 surrounding the bundle of capillary tubes has a length between opposing surfaces 76 and 78 that is greater than the length between the opposing ends 80 and 82 of the capillary tubes. As a result, the banded assembly can be placed on a surface of, for example, an analytical device, without the ends of the capillary tubes touching the surface. In addition, the assemblies can be stacked without disturbing the capillary holding forces in the through holes.

The assembly shown in FIGS. 8 and 9, as with the plates of FIGS. 1–7, can be loaded or filled with a starting liquid sample to provide a plurality of samples, each constituting a portion of the starting liquid sample. Alternatively, the assembly can be loaded with more than one starting liquid sample, with each starting liquid sample filling at least one of the through holes. Herein, by "loaded" or "filled", what is meant is at least partially filled, but not necessarily fully filled. The through-holes can be loaded or filled, for example, by immersing the assembly or plate in a liquid sample, contacting at least one of the opposing surfaces of the assembly or plate with a liquid sample, or contacting the inner walls of the respective through holes with a liquid sample or with respective liquid samples.

Contact between a liquid sample and an opposing surface can be made by flooding, immersing, pipetting, dropping, pouring, or otherwise loading or at least partially filling a plurality of the capillary tubes or through holes such that capillary action pulls portions of the liquid sample into the respective capillary tubes or through holes. Upon removal or discontinued contact of the liquid sample with the assembly or plate, the opposing surfaces of the assembly or plate are preferably made free of liquid sample such that the portions of the sample that remain held within the respective capillary tubes are isolated from one another.

Automated filling devices can be used and are preferred if it is important that the respective liquid samples or liquid sample portions are to only contact the inner walls of the through holes and avoid contacting the opposing surfaces of the assembly.

According to embodiments of the present invention, a high throughput screening method is provided. The method can screen for at least one liquid sample that includes a target component or substance to be analyzed. Herein, the target component or substance to be analyzed may be referred to as an "analyte". The analyte may be, but is not necessarily, a biological sample. The analyte exhibits a detectable property or produces a detectable characteristic in the presence of or upon reaction with a marker compound or the like. For example, the analyte may itself exhibit a fluorescent property. After the liquid sample is at least partially filled into a plurality of the through holes, the portions of the liquid sample that contain the analyte can be detected by determining which of the through holes contains a sample portion that exhibits the fluorescent property.

In another example, the analyte itself does not exhibit a detectable property but may instead cause a marker component to exhibit a detectable property upon reaction with the marker component. According to such an embodiment, the through holes of the testing assembly can be pre-loaded or post-loaded with one or more marker components such that after loading the liquid sample into the plurality of through holes, the sample portions containing an analyte can react with the marker compound and thus enable the marker compound to exhibit a detectable property. In such a case, it is not the analyte itself that exhibits the detectable property, but rather the analyte is detected indirectly as the presence of the analyte causes the detectable property of the marker component which in turn is directly detected. In so doing, the methods of the present invention provide a way to partition and isolate analytes from an original liquid sample.

According to the high throughput screening method, portions of the liquid sample are loaded into a testing assembly having a pair of opposing surfaces and a plurality of through holes, with each of the through holes extending from one of the opposing surfaces to the other of the opposing surfaces. Loading preferably results in at least partially filling a plurality of the through holes with at least portions of the liquid sample, and surface tension holds the respective portions in the respective plurality of through holes. Multiple liquid samples can instead be loaded into respective through holes or into respective pluralities of through holes. The method then involves detecting which of the plurality of sample portions in the through holes exhibit the detectable property.

According to embodiments of the present invention, the high throughput screening assembly preferably comprises at least about 100 through holes, more preferably at least about 500 through holes, and according to some embodiments of the present invention, up to about 1,000,000 through holes. High throughput screening methods can be used in conjunction with these devices to test over 100,000,000 samples or sample portions per assembly per day.

The analyte to be screened may be, for example, a biological cell, a mixture of biological cells, a mutant cell, a secretable protein, an enzyme, a microorganism, a mixture of microorganisms, a contaminant, or combinations thereof. The analyte can be a population of random mutants of one or more organisms. If the analyte is a mixture of biological cells it could be a random sample isolated from a natural environment. The detectable property may be, for example, a fluorescence or adsorption property. Prior to filling the high throughput assembly, the liquid sample may be diluted with a suitable diluent to obtain a concentration of the analyte in the liquid sample such that when the sample is filled into the plurality of through holes, at least one of the analytes is introduced into from about one-quarter to about one-half of the plurality of through holes.

In some cases, it is possible to identify an organism with desirable properties even if the organism is introduced into a plurality of through holes as a mixture with other organisms. Under such conditions, the mixture of other organisms, e.g., mixture of biological cells, may be diluted prior to filling such that several organisms or cells will be introduced into each through hole. Using such a dilution technique, it is possible to detect the presence of an analyte. For example, it is possible to detect one particular mutant from a collection of many biological cells and mutants thereof despite having many cells from the mixture present in each through hole. Thus, for example, if a sample contains 1,000,000 cells and only one of them is a target mutant cell, referred to as the "analyte", and a testing plate having 10,000 through holes is employed, the sample can be diluted such that the 1,000,000 cells fill the through holes with sample portions wherein each portion contains about 100 cells. In cases where the detectable characteristic of the analyte is detectable despite the presence of many other cells within the same through hole, it is possible to isolate the analyte from 99.99% of the sample in a single assay.

The testing plates used in accordance with the present invention, including the plates of FIGS. 1–7 and the assemblies of FIGS. 8 and 9, can comprise hydrophilic materials or coatings, hydrophobic materials or coatings, or a combination thereof to facilitate loading of liquid sample portions into the through holes. For example, the opposing surfaces of the assembly can be made of, or treated with, a hydrophobic material such that liquid samples tend to be repelled from the surface except in areas immediately adjacent the through hole openings on the opposing surface. According to such an embodiment, liquid sample portions can be drawn into the through holes by capillary action without wetting-out onto the opposing surfaces of the plate. As a result, once the plate is loaded with and separated from a liquid sample no fluid communications are provided between individual through holes and contamination of the partitioned sample portions is minimized. According to some embodiments of the present invention, the through holes can include inner walls made of, or coated with, a hydrophilic material that can be easily wetted by an aqueous sample or medium. The entire inner walls of each through hole can be made of or treated with a hydrophilic material or only portions of the inner wall can be so made or treated. Plates having hydrophilic inner walls for the through holes and hydrophobic opposing surfaces provide excellent means to restrain, isolate, or limit the position of liquid samples in the through holes of the testing plate while keeping adjacent surface regions of the opposing surfaces substantially free of liquid sample.

According to some embodiments of the present invention, to facilitate the capillary reaction, it may be desirable to provide a hydrophilic material immediately adjacent the opening to each through hole on an opposing surface while maintaining or providing the remaining area of the opposing surface hydrophobic or non-hydrophilic. Either or both opposing surfaces of the testing plate can be made of or treated with hydrophobic, hydrophilic, or both materials as discussed above although if the through holes are to be loaded by an immersion technique, it is preferred that the opposing surface which will come in contact with the liquid sample is treated with or formed of a hydrophobic material except in areas immediately adjacent and preferably surrounding the through hole openings in the opposing surface.

Exemplary high throughput screening methods that can be used with the assemblies and other plates of the present invention include absorbance transcription assays, fluorescent transcription assays, fluorescent secreted enzyme assays, and microorganism screening assays. These and other suitable assays that can benefit from the plates and methods of the present invention are described, for example, in: Arndt et al., A rapid genetic screening system for identifying gene-specific suppression constructs for use in human cells, *Nucleic Acids Res.*, 28(6): E15 (2000); Rolls et al., A visual screen of a GFP-fusion library identifies a new type of nuclear envelope membrane protein, *J. Cell Biol*, 146(1): 29–44 (1999); Sieweke, Detection of transcription factor partners with a yeast one hybrid screen, Methods Mol. Biol., 130: 59–77 (2000); and WO 97/37036, all of which are herein incorporated in their entireties by reference.

Having thus described the basic concept of the invention, it will be rather apparent to those skilled in the art that the foregoing detailed disclosure is intended to be presented by way of example only, and is not limiting. Various alternations, improvements, and modifications will occur and are intended to those skilled in the art, though not expressly stated herein. These alterations, improvements, and modifications are intended to be suggested hereby, and are within the spirit and scope of the invention. Accordingly, the invention is limited only by the following claims and equivalents thereto.

What is claimed is:

1. An assembly for holding liquid samples, said assembly comprising:
   a substrate having first and second opposing surfaces and including a bundle of capillary tubes, wherein said first opposing surface comprises first ends of the capillary tubes of said bundle and said second opposing surface comprises said second ends of the capillary tubes of said bundle; and
   a plurality of through holes in said substrate, including longitudinally-extending holes through the centers of the capillary tubes of said bundle, each of said through holes extending from an opening in one of the opposing surfaces of the substrate to an opening in the other of the opposing surfaces, wherein the through holes are sized to provide sufficient surface tension by capillary action to hold respective liquid samples.

2. The assembly of claim 1, wherein said bundle further includes a band that bounds the capillary tubes together.

3. The assembly of claim 2, wherein said band comprises metal, plastic, glass, or an elastomeric compound.

4. The assembly of claim 1, wherein each capillary tube of said bundle has a length between the first end and second end thereof that is at least two times greater than the average diameter of said capillary tube.

5. The assembly of claim 1, wherein each capillary tube of said bundle has a length between the first end and second end thereof that is at least four times greater than the average diameter of said capillary tube.

6. The assembly of claim 1, wherein the average diameter of each capillary tube is from about 0.001 millimeter to about one millimeter.

7. The assembly of claim 1, wherein the length of each capillary tube is from about one millimeter to about one centimeter.

8. The assembly of claim 1, wherein each capillary tube has a capacity to hold from about 0.0001 microliter to about ten microliters of liquid sample.

9. The assembly of claim 1, wherein said capillary tubes are fused, bonded or adhered together in said bundle.

10. The assembly of claim 1, wherein said bundle of capillary tubes comprises from about 100 to greater than 1,000 capillary tubes.

11. The assembly of claim 1, wherein said bundle of capillary tubes comprises from about 500 to about 1,500 capillary tubes.

12. The assembly of claim 1, wherein said bundle of capillary tubes has a circular cross-section.

13. The assembly of claim 1, wherein said bundle of capillary tubes comprises a rectangular or square array of capillary tubes.

14. The assembly of claim 1, wherein said bundle of capillary tubes includes capillary tubes arranged in rows and rows of capillary tubes arranged in columns.

15. A method of providing a plurality of liquid samples, said method comprising:
providing the assembly of claim 1,: and
at least partially filling a plurality of said through holes with respective liquid samples, wherein surface tension holds the respective liquid samples in the respective plurality of through holes.

16. The method of claim 15, wherein said at least partially filling comprises contacting at least one of the opposing surfaces of the assembly with at least one liquid sample such that portions of said at least one liquid sample at least partially fill a respective plurality of said through holes.

17. The method of claim 16, further comprising, after said contacting, separating the opposing surfaces of the assembly from said liquid samples such that the surfaces are substantially free of said liquid sample and the portions of said sample held within the respective plurality of through holes are isolated from one another.

18. The method of claim 17, wherein said contacting comprises immersing at least one of said opposing surfaces into said at least one liquid sample.

19. A method for identifying the location of a liquid sample in a testing assembly, said method comprising:
providing the assembly of claim 1 wherein the capillary tubes are arranged in groups, and each of the groups comprises at least two rows of through holes and at least two columns of through holes, and wherein portions of the liquid sample are located in at least some of the through holes;
identifying the liquid sample in at least one through hole; and
locating the identified through hole based upon the group in which the through hole is located.

20. The assembly of claim 1, wherein a plurality of said capillary tubes are filled with respective liquid samples each containing a mixture of biological cells, and wherein at least one of said liquid samples contains at least one analyte cell.

21. A high throughput screening method comprising:
providing at least one liquid sample that includes an analyte that directly or indirectly produces a detectable characteristic;
providing the testing assembly of claim 1;
at least partially filling a plurality of said through holes with at least portions of said at least one liquid sample, wherein surface tension holds the respective portions in the respective plurality of through holes; and
detecting which of said plurality of through holes contains a liquid sample portion that includes said analyte.

22. The method of claim 21, wherein said analyte is a biological cell.

23. The method of claim 21, wherein said detectable characteristic is a fluorescence or absorption characteristic.

24. The method of claim 21, wherein said analyte is at least one of a mutant cell, a secretable protein, an enzyme, or a microorganism.

25. An assembly for holding liquid samples for analysis, said assembly comprising;
a substrate having a pair of opposing surfaces, and side edges;
a plurality of through holes in the substrate each of said through holes extending from an opening in one of the opposing surfaces of the substrate to an opening in the other of the opposing surfaces, said through holes being sized to provide sufficient surface tension by capillary action to hold respective liquid samples; and
a handle connected to said substrate for maneuvering said substrate.

26. The assembly of claim 25, wherein said handle is connected to said substrate with bolts.

27. The assembly of claim 25, wherein an opening is provided in one of said side edges, and an end of said handle is removably positioned within said opening.

28. The assembly of claim 25, wherein said handle extends out from the side of the substrate.

29. An assembly for holding liquid samples for analysis, said assembly comprising:
a substrate having a pair of opposing surfaces;
a plurality of through holes in the substrate, each of said through holes extending from an opening in one of the opposing surfaces of the substrate to an opening in the other of the opposing surfaces, said through holes being sized to provide sufficient surface tension by capillary action to hold respective liquid samples; and
a first evaporation plate secured to one of the opposing surfaces of the substrate, and a second evaporation plate secured to the other of said opposing surfaces of the substrate, said evaporation plates being secured to said substrate to preserve samples dispersed in the through holes from evaporation and contamination.

30. The assembly of claim 29, wherein said evaporation plates are secured to said substrate with clamps.

31. The assembly of claim 29, wherein said evaporation plates are secured to said substrate with bolts.

32. The assembly of claim 29, wherein each of said opposing surfaces includes a recessed portion and said plurality of through holes are located in the recessed portions of the opposing surfaces, and wherein the plurality of through holes in the recessed portions are spaced away from facing surfaces of the evaporation plates when the evaporation plates are secured to the substrate.

33. An assembly for holding liquid samples for analysis, said assembly comprising:
a substrate having a pair of opposing surfaces; and
a plurality of through holes in the substrate, each of said through holes extending from an opening in one of the opposing surfaces of the substrate to an opening in the other one of the opposing surfaces of the substrate, said through holes being sized to provide sufficient surface tension by capillary action to hold respective liquid samples,
wherein a recessed portion having a first depth is provided in a first opposing surface of said pair and a protruding portion having a height is provided on the other opposing surface of said pair, and wherein each of said plurality of through holes extends from the recessed portion of said first opposing surface to the protruding portion of the other opposing surface, and said height is less than said depth.

34. A stackable system comprising two or more of the assemblies of claim 33 stacked together, wherein the protruding portion of one of the assemblies is received within the recessed portion of another of the assemblies.

35. A system comprising two of the assemblies of claim 33 stacked together and further comprising a spacer between the two stacked assemblies.

36. A system comprising at least a first and a second assembly stacked one on top of the other, each assembly comprising:
  a substrate having a first opposing surface and a second opposing surface; and
  a plurality of through holes in the substrate, each of said through holes extending from an opening in the first opposing surface of the substrate to an opening in the second opposing surface of the substrate, said through holes being sized to provide sufficient surface tension by capillary action to hold respective liquid sample, and
  wherein said system further comprises an evaporation plate disposed between said first assembly and said second assembly, said evaporation plate having a first surface facing the second opposing surface of said first assembly, and said evaporation plate having a second surface facing the first opposing surface of said second assembly, and wherein at least one of the surfaces of said evaporation plate is provided with a recessed portion to space the surface of the recessed portion from ends of the through holes at one or both of the second opposing surface of the first assembly and the first opposing surface of the second assembly.

37. The system of claim 36, wherein the second opposing surface of said first assembly is provided with a recessed portion.

38. The system of claim 36, wherein the first opposing surface of said second assembly is provided with a recessed portion.

39. The system of claim 36, wherein both the first and second surfaces of said evaporation plate are provided with a recessed portion.

40. A system comprising at least a first and a second assembly stacked one on top of the other, each assembly comprising:
  a substrate having a first opposing surface and a second opposing surface; and
  a plurality of through holes in the substrate, each of said through holes extending from an opening in the first opposing surface of the substrate to an opening in the second opposing surface of the substrate, said through holes being sized to provide sufficient surface tension by capillary action to hold respective liquid sample, and
  wherein said system further comprises an evaporation plate disposed between said first assembly and said second assembly, said evaporation plate having a first surface facing the second opposing surface of said first assembly, and said evaporation plate having a second surface facing the first opposing surface of said second assembly, and wherein at least one of the second opposing surface of said first assembly and the first opposing surface of said second is provided with a recessed portion to space ends of the through holes at one or both of the second opposing surface of the first assembly and the first opposing surface of the second assembly, from the evaporation plate.

41. The system of claim 40, wherein the second opposing surface of said first assembly is provided with a recessed portion.

42. The system of claim 40, wherein the first opposing surface of said second assembly is provided with a recessed portion.

43. The system of claim 40, wherein both the second opposing surface of said first assembly and the first opposing surface of said second assembly are provided with a recessed portion.

44. The system of claim 40, wherein at least one of the first and second surfaces of said evaporation plate is provided with a recessed portion.

45. The system of claim 40, wherein a spacer is provide between the evaporation plate and at least one of said first and second assemblies.

46. A system comprising two or more assemblies stacked one on top of the other, each assembly comprising:
  a substrate having a first opposing surface and a second opposing surface; and
  a plurality of through holes in the substrate, each of said through holes extending from an opening in the first opposing surface of the substrate to an opening in the second opposing surface of the substrate, said through holes being sized to provide sufficient surface tension by capillary action to hold respective liquid sample, and
  wherein said system further comprises an evaporation plate disposed between said first assembly and said second assembly, said evaporation plate having a first surface facing the second opposing surface of said first assembly, said evaporation plate having a second surface facing the first opposing surface of said second assembly, and wherein a spacer is provided between at least one of the second surfaces of said evaporation plate and at least one of the first and second assemblies, said spacer spacing openings of the through holes away from the evaporation plate.

47. The system of claim 46, wherein a spacer is disposed between the second opposing surface of said first assembly and the evaporation plate.

48. The system of claim 46, wherein a spacer is disposed between the first opposing surface of said second assembly and the evaporation plate.

49. The system of claim 46, wherein at least one of said surfaces of said evaporation plate is provided with a recessed portion.

50. A plate for holding samples of a solution with biological material for analysis, said plate comprising;
  a platform having a pair of opposing surfaces; and
  a plurality of holes in the platform, each of said holes extending from an opening in one of the opposing surfaces of the platform to an opening in the other one of the opposing surfaces of the platform, each of the holes being sized to hold biological material in said through holes by surface tension; and
  wherein at least one of the opposing surfaces is provided with a recessed portion.

51. The plate of claim 50, wherein both opposing surfaces are provided with a recessed portion.

52. The plate of claim 50, wherein the plurality of holes contains portions of a sample of a biological material, the biological material includes cells, and each of the holes is sized to hold a plurality of the cells.

53. The plate of claim 50, wherein the holes are arranged in groups on the substrate, each of the groups comprises at least two rows of holes and at least two columns of holes.

54. An assembly comprising two or more of the plates of claim 50 stacked one on top of the other.

55. The assembly of claim 54, wherein a spacer is provided between at least two of the plates of said assembly.

56. The assembly of claim 54, wherein at least one of said plates of said assembly is provided with a handle.

57. A high throughput screening method comprising:
providing at least one liquid sample that includes an analyte that directly or indirectly produces a detectable characteristic in one or more of an absorbance transcription assay, a fluorescent transcription assay, a fluorescent secreted enzyme assay, and a microorganism screening assay;
providing the assembly of claim 1;
at least partially filling a plurality of said through holes of said assembly with at least portions of said at least one liquid sample, wherein surface tension holds the respective portions in the respective plurality of through holes; and
detecting which of said plurality of through holes contains a liquid sample portion that includes said analyte.

58. The method of claim 57, wherein said detectable characteristic is produced in an absorbance transcription assay.

59. The method of claim 57, wherein said detectable characteristic is produced in a fluorescent transcription assay.

60. The method of claim 57, wherein said detectable characteristic is produced in a fluorescent secreted enzyme assay.

61. The method of claim 57, wherein said detectable characteristic is produced in a microorganism screening assay.

62. A high throughput screening method comprising:
providing at least one liquid sample that includes an analyte that directly or indirectly produces a detectable characteristic in one or more of an absorbance transcription assay, a fluorescent transcription assay, a fluorescent secreted enzyme assay, and a microorganism screening assay;
providing the assembly of claim 25;
at least partially filling a plurality of said through holes with at least portions of said at least one liquid sample, wherein surface tension holds the respective portions in the respective plurality of through holes; and
detecting which of said plurality of through holes contains a liquid sample portion that includes said analyte.

63. The method of claim 62, wherein said detectable characteristic is produced in an absorbance transcription assay.

64. The method of claim 62, wherein said detectable characteristic is produced in a fluorescent transcription assay.

65. The method of claim 62, wherein said detectable characteristic is produced in a fluorescent secreted enzyme assay.

66. The method of claim 62, wherein said detectable characteristic is produced in a microorganism screening assay.

67. A high throughput screening method comprising:
providing at least one liquid sample that includes an analyte that directly or indirectly produces a detectable characteristic in one or more of an absorbance transcription assay, a fluorescent transcription assay, a fluorescent secreted enzyme assay, and a microorganism screening assay;
providing the assembly of claim 29;
at least partially filling a plurality of said through holes with at least portions of said at least one liquid sample, wherein surface tension holds the respective portions in the respective plurality of through holes; and
detecting which of said plurality of through holes contains a liquid sample portion that includes said analyte.

68. The method of claim 67, wherein said detectable characteristic is produced in an absorbance transcription assay.

69. The method of claim 67, wherein said detectable characteristic is produced in a fluorescent transcription assay.

70. The method of claim 67, wherein said detectable characteristic is produced in a fluorescent secreted enzyme assay.

71. The method of claim 67, wherein said detectable characteristic is produced in a microorganism screening assay.

72. A high throughput screening method comprising:
providing at least one liquid sample that includes an analyte that directly or indirectly produces a detectable characteristic in one or more of an absorbance transcription assay, a fluorescent transcription assay, a fluorescent secreted enzyme assay, and a microorganism screening assay;
providing the assembly of claim 33;
at least partially filling a plurality of said through holes with at least portions of said at least one liquid sample, wherein surface tension holds the respective portions in the respective plurality of through holes; and
detecting which of said plurality of through holes contains a liquid sample portion that includes said analyte.

73. The method of claim 72, wherein said detectable characteristic is produced in an absorbance transcription assay.

74. The method of claim 72, wherein said detectable characteristic is produced in a fluorescent transcription assay.

75. The method of claim 72, wherein said detectable characteristic is produced in a fluorescent secreted enzyme assay.

76. The method of claim 72, wherein said detectable characteristic is produced in a microorganism screening assay.

77. A high throughput screening method comprising:
providing at least one liquid sample that includes an analyte that directly or indirectly produces a detectable characteristic in one or more of an absorbance transcription assay, a fluorescent transcription assay, a fluorescent secreted enzyme assay, and a microorganism screening assay;
providing the plate of claim 50;
at least partially filling a plurality of said through holes with at least portions of said at least one liquid sample, wherein surface tension holds the respective portions in the respective plurality of through holes; and
detecting which of said plurality of through holes contains a liquid sample portion that includes said analyte.

78. The method of claim 77, wherein said detectable characteristic is produced in an absorbance transcription assay.

79. The method of claim 77, wherein said detectable characteristic is produced in a fluorescent transcription assay.

80. The method of claim 77, wherein said detectable characteristic is produced in a fluorescent secreted enzyme assay.

81. The method of claim 77, wherein said detectable characteristic is produced in a microorganism screening assay.

* * * * *